United States Patent [19]

Lukacs et al.

[11] 3,963,119

[45] June 15, 1976

[54] SERUM SEPARATING APPARATUS

[75] Inventors: Michel J. Lukacs, Goshen; Ian H. Jacoby, Middletown, both of N.Y.

[73] Assignee: Lucaks and Jacoby Associates, Middletown, N.Y.

[22] Filed: Sept. 16, 1974

[21] Appl. No.: 505,992

Related U.S. Application Data

[60] Continuation of Ser. No. 411,287, Oct. 13, 1973, abandoned, which is a division of Ser. No. 270,278, July 10, 1972, Pat. No. 3,780,935.

[52] U.S. Cl. ................................ 206/216; 23/259; 128/272; 210/DIG. 23; 210/516; 206/525; 233/1 A; 233/26; 252/60; 141/311 R
[51] Int. Cl.² ....................................... B01D 21/26
[58] Field of Search .............. 23/230 B, 258.5, 259, 23/292; 128/2 F, 214 R, 218 M, 272; 210/83, 84, 205, 514–518, DIG. 23, DIG. 24; 233/1 A, 1 R, 26; 141/311; 206/525, 216; 252/60

[56] References Cited
UNITED STATES PATENTS 3,852,194    12/1974    Zine, Jr. ...................... 210/DIG. 23

OTHER PUBLICATIONS

Cancer, 12: 590–595 595 (1959).

Journal of Urology 85: 1006–1010 1010 (1961).

Blood 18: 89–94 94 (1961).

Primary Examiner—John Adee
Assistant Examiner—Robert G. Mukai

[57]    ABSTRACT

The separation of a sample of blood into serum and clot portions is accomplished by means of a sealant consisting essentially of a silicone fluid and silica dispersed therein. The separation is accomplished by inserting a device containing a supply of the sealant into a container holding a sample of the blood, the device being characterized by a nozzle portion which extends into the sample. The container and device are centrifuged so that it separates into serum and clot portions and the sealant, having a specific gravity of at least 1.026, separates the two portions.

11 Claims, 8 Drawing Figures

SERUM SEPARATING APPARATUS

CROSS-REFERENCE TO RELATED APPLICATIONS

This is a continuation of copending U.S. patent application Ser. No. 411,287, filed Oct. 13, 1973, and now abandoned; which application is a division of copending application Ser. No. 270,278, filed July 10, 1972, and now U.S. Pat. No. 3,789,935, the disclosure of both said applications being incorporated herein by reference.

BACKGROUND OF THE INVENTION

This invention relates to apparatus for separating a blood sample by centrifuging into clot portions, so that the serum may be quickly and readily removed without contamination by the clot portion.

In recent years, biomedical and hospital laboratories have been faced with increasing demands for more and more routine, as well as specialized, diagnostic tests of blood samples, To meet the demands of these tests equipment has been devised which automatically takes a sample or specimen of blood which has been placed in a cup and subjects it to a series of programmed tests which eventuate in a readout on a record member. While these analyzers have increased the efficiency of performing the necessary tests, a problem has continued in finding ways and means of separating the serum from the clot portion and removing the serum for analysis. Various types of tube and plug devices have been suggested by the prior art. For example, in U.S. Pat. No. 3,512,940, issued May 19, 1970, a device consisting of a tube with a filter at one end thereof is inserted into a second but larger diameter tube containing a sample of the material desired to be filtered. In U.S. Pat. No. 3,508,653, issued Apr. 28, 1970, a piston in the form of a solid plug is driven through a centrifuged blood sample so as to position itself between the serum and clot portions of the centrifuged sample. The tube within the tube concept of U.S. Pat. No. 3,512,940 suffers from the apparent deficiency of being costly and not readily adaptable for disposal after a single use. The plug arrangement of U.S. Pat. No. 3,508,653 has the shortcoming of utilizing a solid plug member which when subjected to a substantial centrifugal force, may also develop radial forces acting against the side of the sample tube, thus creating the danger of breakage.

SUMMARY OF THE INVENTION

The present inventin provides apparatus by which the serum and clot portions of the blood sample are separated quickly and effectively by use of a simple device containing a liquid sealant consisting essentially of a silicone fluid and silica. The sealant has a specific gravity of at least 1.026 and preferably in the range of 1.030 to 1.050. As such, it will normally be at the proper specific gravity to divide the serum and clot portions of the centrifuged sample, sealing the clot in the container while the serum is removed.

Accordingly, it is an object of the present invention to provide a simple and effective method of obtaining a serum sample during centrifuging. It is a further object of the present invention to provide an apparatus for carrying out the separation technique. Yet another object of the present invention is to provide a device for dispensing the sealant which is of such low cost that the device may be discarded after a single use.

DESCRIPTION OF THE ILLUSTRATED EMBODIMENT

Figure 1:
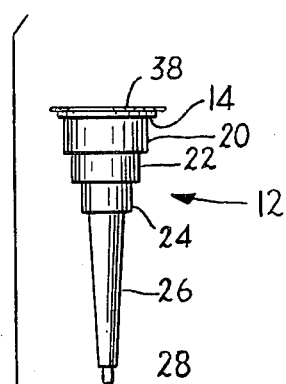
FIG. 1 is an exploded partially sectional view of a sample tube and dispenser in accordance with the present invention.
Figure 2:
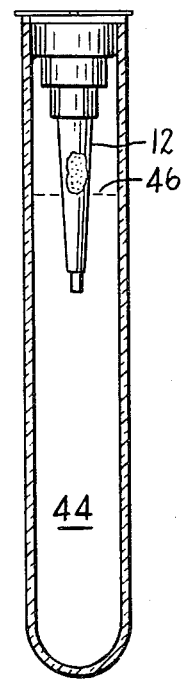
FIG. 2 is a partially sectional side view of a sample tube and dispenser in accordance with the present invention with the dispenser inserted into a supply of blood.
Figure 3:
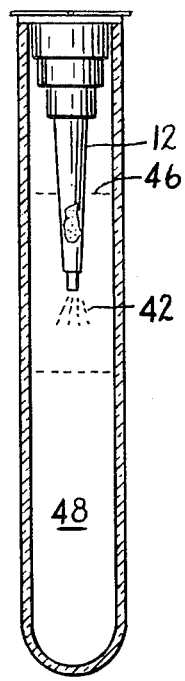
FIG. 3 is a partially sectional view similar to that of FIG. 2 wherein the blood, sample tube and dispenser have been partially subjected to centrifuging.
Figure 4:
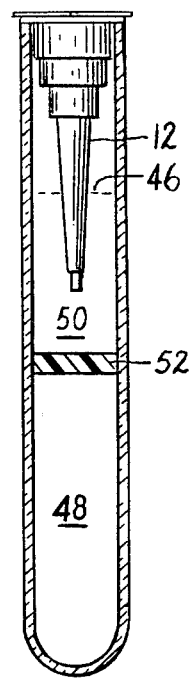
FIG. 4 is a view similar to FIG. 2 wherein the blood, the sample tube and dispenser have been subjected to the complete centrifuging step.
Figure 5:
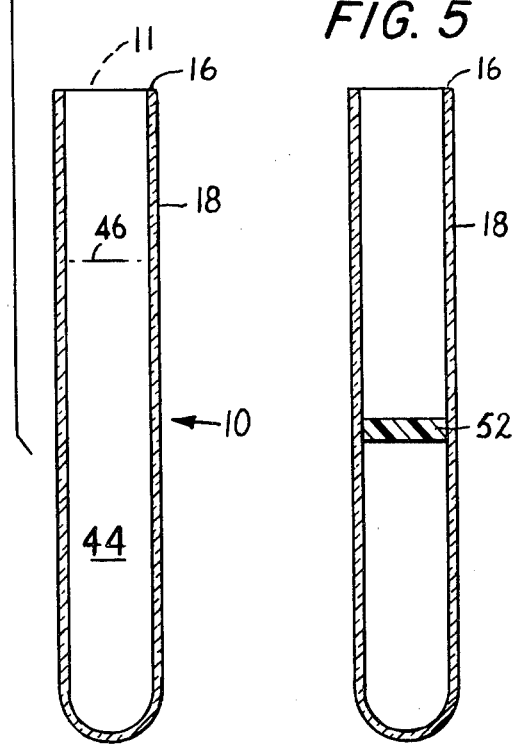
FIG. 5 is a sectional view of the sample tube with the separator in place overlying the clot portion with the serum portion removed.

Referring to the drawings, a container 10 for holding a blood sample is illustrated as a straight side wall sample tube 10 with an open top end 11. Into the open top 11 is inserted a dispenser 12. The dispenser 12 has a flange member 14 which overlies the top edge 16 of the side wall 18 of the container. The dispenser 12 includes a body portion 19 consisting of three ring sections 20, 22 and 24. Extending from the body 19 is an elongated nozzle portion 26 and at the end of the nozzle 26 is a tip 28 having an opening 30 therein. The purpose of the three rings 20, 22 and 24 is to permit the dispenser 12 to be used with containers of various diameters. Ring 20 has a shoulder 32 and a side wall 33, ring 22 a shoulder 34 and a side wall 35, and ring 24 has a shoulder 36 and a side wall 37. When using a narrow container, the dispenser bears on the top edge of the side wall of the container at one of the shoulders 32, 34 or 36 and the side wall of the next smaller ring is parallel with the inner side wall of the container. During centrifuging the relationship between the inner surface of the container and the side wall of the ring insures stability of the dispenser during this period.

By utilizing a dispenser as illustrated herein, it is possible to use one dispenser for varying diameter containers.

The body portion 19 of the dispenser has an open end 37 over which is placed a seal 38. The seal 38 has a small opening 40 therein. The seal 38 is not placed over the open end until a sealant 42 has been placed in the dispenser.

The sealant 42 consists essentially of a silicone fluid with an inert filler, such as silica, dispersed therein. The sealant should have a specific gravity of at least 1.026 and preferably in the range of 1.030 to 1.050.

The normal specific gravity of blood as determined by the pycnometric method is considered to be in the range of 1.048 to 1.066 with averages of 1.052 to 1.063. After centrifuging the specific gravity of the blood serum which separates from the remainder of the blood is at least 1.026 and in the range of 1.026 to 1.031. The specific gravity of the heavier portions such as the erythrocytes is 1.092 to 1.095.

In selecting a sealant it is necessary to select one which has a specific gravity greater than that of the serum portion. Accordingly, the sealant should have a specific gravity of at least 1.026. However, its specific gravity should not be too high so as to cause it to layer somewhere in the clot portion. Such layering would be of no practical use towards obtaining a separated serum portion. A preferred sealant would have a specific gravity in the range of 1.030 to 1.050.

The sealant is also preferably thioxtropic, water insoluble, substantially non-toxic as well as substantially chemically inert with respect to the constituents of the blood sample, particularly those in the serum portion.

A preferred sealant formulation is as follows:

Example I

|  | Parts by weight |
| --- | --- |
| Silicone fluid (dimethylpolysiloxane) | 100 |
| Silica (specific gravity 2.65) | 8 |
| Silica (specific gravity 2.3) | 6 |

The silicone fluid used in Example I was a dimethylpolysiloxane polymer made by Union Carbode Corporation and identified by the designation "L-45". It had a viscosity of 12,500 centistokes and a specific gravity of about 0.973 at 25°C. The silica with a specific gravity of 2.65 was an amorphous silica having a particle size of at least 75% being less than 5.0 microns. It was made by Whittaker, Clark & Daniels and identified by the designation "No. 31 Lo Micron". The silica with a specific gravity of 2.3 was a hydrophobic amorphous silica having an average particle size of about 20 millimicrons. It was made by Degussa Inc. and identified by the designation "Aerosil R 972".

The silicone fluid and the silica were mixed together to a thixotropic condition with a resultant specific gravity of 1.045 to 1.050 to form the sealant.

Figure 6:
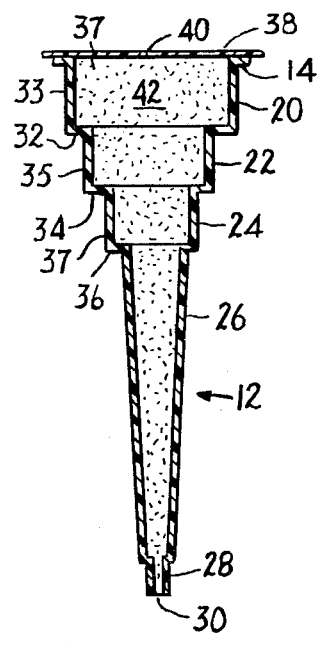
FIG. 6 is an enlarged sectional view of the sealant dispenser showing the sealant contained therein.
Figure 7:
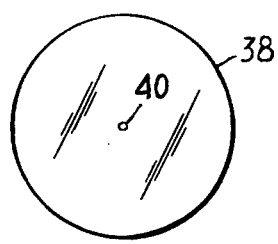
FIG. 7 is a top view of the dispenser of FIG. 6.
Figure 8:
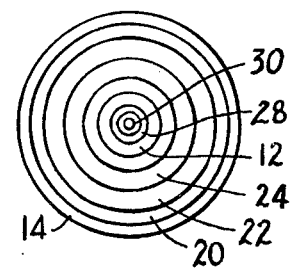
FIG. 8 is a bottom view of the dispenser of FIG. 6.

The sealant was then placed in a dispenser of the type illustrated in FIG. 6 in particular. The diameter of the flange was 0.70 inches and the overall length 1.75 inches with the nozzle and tip being 1.10 inches. The opening in the tip was 0.032 inches. The filled dispenser was placed in a standard sample tube having an overall length of 3.875 inches with the shoulder 32 of the first ring resting on the top of the tube side wall. The tube had previously been filled with a whole blood specimen to within 1.10 inches of the open end of the tube. The extent of the dispenser from shoulder 32 to the end of the tip was 1.5 inches. Thus, the dispenser tip and part of the nozzle extended well into the blood sample.

The tube with the blood sample and dispenser was centrifuged for approximately 10 minutes. After 5 minutes substantially all of the sealant had passed from the dispenser. The sealant did not disperse but instead remained homogeneous and settled as a layer between the serum and clot portions of the centrifuged blood. It was noted that the sealant settled as a substantially even layer between the two portions since its specific gravity of 1.045 to 1.050 was less than that of the clot portion and greater than that of the serum portion. The sealant formed a tight seal against the inner wall of the tube. Also noted was the fact that the sealant had mixed into it, particularly in the portion near the clot portion, fibrant matter which had been filtered out of the serum portion as the sealant settled to its own specific gravity level.

The use of the dispenser which extended into the blood sample expedited the procedure since it was not necessary for the sealant to overcome the surface tension of the blood sample.

With the sealant in place it was possible to merely decant off the serum portion with the clot being trapped behind the sealant.

The specific gravity of the sealant was determined by using a copper sulfate method. The procedure consists of letting drops of the sealant fall into a graded series of solutions of copper sulfate of known specific gravity and noting whether the drops rise or fall. The series used were graded at 0.005 intervals. Merely by observing the drops it was possible to determine that the sealant had a specific gravity between 1.045 and 1.050.

Another sealant formulation is as follows:

Example II

|  | Parts by weight |
| --- | --- |
| Silicone fluid (dimethylpolysiloxane) | 100 |
| Silica (specific gravity 1.95) | 14 |

The silicone fluid of Example II is the same dimethylpolysiloxane polymer of Example I. The silica with a specific gravity of 1.95 has an average particle size of 16 millimicrons. It is made by Henlig & Co. and identified by the designation "TRI-SIL 404". The specific gravity of the sealant is from 1.045 to 1.050.

In selecting silicone fluids and fillers, one should select materials which when mixed together will give the desired specific gravity, be substantially non-toxic, water insoluble and substantially chemically inert with respect to the constituents of at least the serum portion.

The dispenser serves to meter out the sealant gradually and this gradual metering provides sufficient lead time for the centrifugation to take effect before the sealant is in place. If the sealant were allowed to be positioned too soon some unwanted matter, such as red cells or fibrilar like material, may be trapped in the serum portion by the sealant.

While various examples of the sealant have been described herein and one embodiment of the dispenser illustrated in the drawings, those skilled in the art may practice the invention in its various forms by other embodiments without departing from the scope of the claims herein.

What is claimed:

1. A dispensing device for holding and dispensing a supply of a sealant used as a separator between serum and clot portions of a blood sample obtained during centrifuging of the sample in an open ended container, said device including:

a hollow body portion holding a supply of sealant therein;

said sealant comprising a supply of thixotropic, water insoluble, substantially non-toxic material consisting essentially of a silicone fluid and an inert filler dispersed therein, said sealant having a specific gravity in the range of 1.026 to 1.092;

said hollow body portion including an integrally formed elongated narrow nozzle portion extending therefrom and containing a portion of the sealant material;

said nozzle having a free end portion adapted to extend into a container having a blood sample therein, said free end portion having an opening therein through which the sealant is dispensed during centrifuging;

said body having an integrally formed annular shoulder extending from the end thereof opposite the free end portion of the nozzle and an annular side wall extending therefrom towards the nozzle, said shoulder being adapted to engage the opened end of the container for supporting the device in said container, with the side wall of the device received within the container for stabilizing the device therein during centrifuging, whereby upon centrifuging of the blood sample in the container with said device mounted therein, said sealant will separate the blood into serum and clot portions and form a separator between said serum and clot portions of the centrifuged sample.

2. A device as defined in claim 1 wherein the body portion has an open end opposite the nozzle portion and further includes a cover member extending across said open end.

3. A device as defined in claim 1 wherein said annular side wall of said body portion is stepped longitudinally along its length to define a plurality of annular shoulders for supporting said device in open end containers of different diameters.

4. A device as defined in claim 1 wherein said nozzle comprises a narrow elongated and slightly tapered hollow tube adapted to extend into the sample of blood in the containers.

5. A container and sealant dispensing combination for use with a supply of blood to be separated into serum and clot portions by centrifuging, said combination including:

a side walled container having opposite open and closed ends;

a supply of sealant and a dispensing device therefor inserted into said container through the open end;

said sealant comprising a supply of thixotropic water insoluble material, substantially non-toxic and substantially chemically inert with respect to the constituents of the serum portion of the blood sample and comprising a silicone fluid and a filler, said sealant having a specific gravity in the range of about 1.026 and 1.092; and said dispensing device providing means for metering out the sealant during centrifuging whereby said sealant forms a layer between the serum portion and the clot portion and a tight seal against the inner side wall of the container so that the serum portion may be removed from the container.

6. A device for use with a supply of blood to be separated into serum and clot portions by centrifuging, said device comprising, in combination, a container for said blood sample having opposed open and closed ends and a peripheral side wall extending therebetween; and a supply of sealant and a dispensing device therefor in said container; said sealant comprising a supply of thixotropic water insoluble, substantially non-toxic material comprising a silicone fluid and a filler, said sealant having a specific gravity in the range of about 1.026 to 1.092 and being substantially chemically inert with respect to the constituents of the serum portion of the blood sample; said dispensing device providing means for distributing the sealant through the blood sample during centrifuging whereby the blood will separte into serum and clot portions and the sealant will form a barrier layer between the serum and clot portions.

7. A container and sealant combination for use with a supply of blood to be separated into serum and clot portions by centrifuging, said combination including:

a side walled container having opposite open and closed ends;

a supply of sealant inserted into said container through the open end thereof;

said sealant comprising a supply of thixotropic water insoluble material, substantially chemically inert with respect to the constituents of the serum portion of the blood sample comprising a silicone fluid and a filler; and said sealant having a specific gravity in the range of about 1.026 to 1.092, whereby during centrifuging said sealant forms a layer between the serum portion and the clot portions of the blood and a tight seal against the inner surface of the side wall of the container so that the serum portion may be removed from the container.

8. The container and sealant combination as defined in claim 7 wherein said thixotropic material consists essentially of a silicone fluid and an inert filler dispersed therein.

9. A container and sealant combination for use with a supply of blood to be separated into serum and clot portions by centrifugation and adapted to form a substantially complete physical seal between the separated serum and clot portions; said combination comprising:

a container having an open end, an opposed closed end, and a side wall extending therebetween for retaining a supply of blood; and a supply of sealant located within said container;

said sealant comprising a supply of thixotropic water insoluble material substantially chemically inert with respect to the constituents of the serum portion of the blood sample and comprising a silicone fluid and a filler, said sealant having a specific gravity in the range of about 1.026 to 1.092 whereby in response to centrifugation, said sealant moves to a position in the container intermediate the serum and clot portions of the blood sample to physically separate the same while forming a relatively tight, fixed seal against the inner surface of the container.

10. A container and sealant combination containing a supply of blood separated by centrifugation into serum and clot portions of differing specific gravities comprising:

a side walled container having opposite open and closed end portions containing a blood sample centrifugally separated into serum and clot portions; and a layer of sealant in said container between said centrifugally separated serum and clot portions forming a relatively tight, fixed seal against the inner surface of the side wall of the container while separating said serum and clot portions;

said sealant comprising a supply of thixotropic water insoluble material substantially chemically inert with respect to the constituents of the serum portion of the blood and comprising a silicone fluid and a filler, said sealant having a specific gravity in the range of about 1.026 to 1.092 whereby said layer of sealant is positioned between the serum and clot portions of the blood during centrifuging.

11. A seal for physically separating the serum and clot portions of a blood sample in a container; said seal comprising a layer of thixotropic water insoluble material substantially chemically inert with respect to the constituents of the serum portion of the blood and comprising a silicone fluid and a filler, said sealant having a specific gravity in the range of about 1.026 to 1.092 and forming a relatively tight, fixed seal against the inner surface of the container at a position between the separated serum and clot portions thereby physically separating the serum and clot portions and enabling the serum portion to be removed by decanting.

* * * * *